United States Patent
Götz et al.

(10) Patent No.: US 7,550,648 B2
(45) Date of Patent: Jun. 23, 2009

(54) INDUCING NEUROFIBRILLARY TANGLES IN TRANSGENIC MICE EXPRESSING A MUTANT TAU PROTEIN

(75) Inventors: Jürgen Götz, Zürich (CH); Roger Nitsch, Zollikon (CH); Feng Chen, Zürich (CH)

(73) Assignee: Universitat Zurich, Zurich (CH)

( * ) Notice: Subject to any disclaimer, the term of this patent is extended or adjusted under 35 U.S.C. 154(b) by 0 days.

(21) Appl. No.: 11/976,318

(22) Filed: Oct. 23, 2007

(65) Prior Publication Data

US 2008/0261878 A1   Oct. 23, 2008

Related U.S. Application Data

(63) Continuation of application No. 10/487,546, filed as application No. PCT/EP02/09491 on Aug. 24, 2002, now abandoned.

(60) Provisional application No. 60/314,303, filed on Aug. 24, 2001.

(30) Foreign Application Priority Data

Aug. 24, 2001   (EP)   ................................ 01120348

(51) Int. Cl.
*G01N 33/00* (2006.01)
*A01K 67/033* (2006.01)

(52) U.S. Cl. ............................... 800/12; 800/3; 800/18
(58) Field of Classification Search ........................ None
See application file for complete search history.

(56) References Cited

U.S. PATENT DOCUMENTS 6,172,277 B1 * 1/2001 Tate et al. ..................... 800/12
6,664,443 B1 * 12/2003 Hutton et al. .................. 800/12

FOREIGN PATENT DOCUMENTS

WO   99/57129   11/1999

OTHER PUBLICATIONS

Lannfelt et al. Alzheimer's Disease: Molecular Genetics and Transgenic Animal Models. Behav. Brain Res., 1993, vol. 57, pp. 207-213.*

Higgins et al. Transgenic mice expressing human beta-APP751, but not mice expressing beta-APP695, display early Alzheimer's disease-like histopathology. Annals NY Acad. Sci.1993, vol. 695, pp. 224-227.*

Felsenstein et al. Transgenic Rat and In-Vitro Studies of β-Amyloid Precursor Protein Processing. Hanin, I. et al., eds., Advances in Behavioral Biology: Alzheimer's and Parkinson's diseases: Recent developments. Publisher: Plenum Press, 1995, pp. 401-405.*

Podlisny e al. Synthetic Amyloid Beta Protein Fails to Produce specific Neurotozicity in Monkey Cerebral Cortex. Neuro. Biol. Aging. 1992, vol. 13, pp. 561-567.*

Frautschy et al., "Effects of injected Alzheimer β-amyloid cores in rat brain". Proc. Natl. Acad. Sci. USA 88 (1991), 8362-8366.

Games et al., "Alzheimer-type neuropathology in transgenic mice overexpressing V717F β-amyloid precursor protein". Nature 373 (1995), 523-527.

Götz et al., "Formation of Neurofibrillary Tangles in P301L Tau Transgenic Mice Induced by A β42 Fibrils". Science 293 (2001), 1491-1495.

Götz et al., "Tau and transgenic animal models". Brain Research Reviews 35 (2001), 266-286.

Götz et al., "Tau Filament Formation in Transgenic Mice Expressing P301L Tau". The Journal of Biochemistry Chemistry 276:1 (2001), 529-534.

Lewis et al., "Neurofibrillary tangles, amytotrophy and progressive motor disturbance in mice expressing mutant (P301L) tau protein". Nature Genetics 25 (2000), 402-405.

* cited by examiner

*Primary Examiner*—Deborah Crouch
(74) *Attorney, Agent, or Firm*—Jacobson Holman PLLC (57) ABSTRACT

The present invention discloses a method and an in-vivo assay system useful for the identification and testing of modulating agents as well as for the validation of therapies of neurodegenerative diseases associated with the formation of neurofibrillary tangles, in particular Alzheimer's disease. The present invention is based on the surprising finding that injection of β-amyloid $A\beta_{42}$ fibrils into brains of P301L mutant tau transgenic mice caused several-fold increases in the numbers and an accelerated production of neurofibrillary tangles in cell bodies predominantly within the amygdala. The induced neurofibrillary tangles occurred as early as 18 days after $A\beta_{42}$ injections and displayed striking features of neurofibrillary tangles of several human neurodegenerative diseases, particularly Alzheimer's disease.

24 Claims, 11 Drawing Sheets

Fig. 1: Stereotaxic injection of aggregated Aβ42 into cortex and CA1 region of the hippocampus

Fig. 2: Tangle formation after injection of Aβ42 fibrils

B

Aβ42-1
(reverse control peptide)

A

Aβ42 fibrils

Fig. 4 : Presence of NFTs and neuropil threads in the amygdala after triggering with Aβ42 fibrils P301L tau transgenic brain Fig. 5: NFTs in the amygdala and cortex of tau transgenic mice induced by Aβ42 fibrils Fig. 6: Aβ42 fibrils trigger NFT formation in the amygdala, similar to NFTs in human AD brains A  P301L tau transgenic brain B  human AD brain Figure 7: AD-like tau filaments in the amygdala after triggering with Aβ42 fibrils Fig. 9: Role of phosphorylation in NFT formation

INDUCING NEUROFIBRILLARY TANGLES IN TRANSGENIC MICE EXPRESSING A MUTANT TAU PROTEIN

This is a continuation of Ser. No. 10/487,546, filed, Aug. 23, 2004, now abandoned which is a 371 of PCT/EP02/09491, filed Aug. 24, 2002, which claims the benefit of U.S. Provisional Application No. 60/314,303, filed Aug. 24, 2001.

The present invention relates to a method of inducing the formation of neurofibrillary tangles in transgenic non-human animals and said animals as such. An in-vivo assay is provided whereby compounds and modifying agents can be tested and validated for their potential efficacy as therapeutics for the treatment of disorders associated with neurofibrillary tangles, in particular Alzheimer's disease and other tauopathies.

Neurodegenerative diseases, in particular Alzheimer's disease, have a severely debilitating impact on a patient's life. Furthermore, these diseases constitute an enormous health, social, and economic burden. Alzheimer's disease is the most common age-related neurodegenerative condition affecting about 10% of the population over 65 years of age and up to 45% over age 85 (for a recent review see Vickers et al., *Progress in Neurobiology* 2000, 60:139). Presently, this amounts to an estimated 12 million cases in the US, Europe, and Japan. This situation will inevitably worsen with the demographic increase in the number of old people ("aging of the baby boomers") in developed countries. The neuropathological hallmarks that occur in the brains of individuals suffering from Alzheimer's disease are senile plaques, composed of amyloid-β protein, and profound cytoskeletal changes coinciding with the appearance of abnormal filamentous structures and the formation of neurofibrillary tangles. AD is a progressive disease that is associated with early deficits in memory formation and ultimately leads to the complete erosion of higher cognitive function. Currently, there is no cure for AD, nor is there an effective treatment to halt the progression of AD or even a method to diagnose AD ante-mortem with high probability. The late onset and complex pathogenesis of neurodegenerative disorders pose a formidable challenge to the development of therapeutic and diagnostic agents. Therefore, it is very important to develop suitable animal models and in-vivo assay systems of neurodegenerative disease which may be useful in the development and subsequent validation of such therapeutic and diagnostic agents.

The pathology of Alzheimer's disease is characterized by two hallmarks: senile plaques composed of proteinaceous deposits of β-amyloid peptide and neurofibrillary tangles composed of tau protein. Currently, it is still controversial which of these histopathological features more closely relates to the primary cause of neurodegeneration in Alzheimer's disease. Tauopathies, in general, are characterized by neuronal and/or glial tau inclusions, insoluble deposits comprising tau or tau-similar structures, the appearance of abnormal filamentous neuronal structures, structures of straight tau filaments, and the formation of neurofibrillary tangles composed of paired helical filaments. Tau is a microtubule-associated protein of low molecular weight and is predominantly expressed in the axons of the CNS and to a lesser extent in axons of the peripheral nervous system, whereas in astrocytes and oligodendrocytes they are hardly expressed at all. Alternative splicing of the gene coding for tau results in a number of isoforms present in the adult human brain. The splicing event is developmentally regulated. In fetal brain only the shortest isoforms are expressed, whereas all six tau-isoforms of 352 up to 441 amino acids in length exist in the postnatal human brain. They differ in the extent of tandem repeat sequences in the C-terminal region. For instance, the 3R-tau and 4R-tau isoforms consist of either three or four repeat sequences of 31 and 32 amino acids each. Tau proteins bind to and stabilize microtubules and promote their polymerization. Binding of microtubules by tau is due to highly conserved amino acid motifs localized in the carboxy-terminal part of the protein. The 4R-tau isoforms have a higher binding affinity for microtubules and are more active in promoting their assembly than the 3R-tau isoforms. One of the most striking features of tau proteins is phosphorylation, which occurs at about 30 of 79 potential serine (Ser) and threonine (Thr) phosphorylation sites. The degree of phosphorylation declines with age. Consequently, in fetal CNS tau protein is higher phosphorylated as in adult CNS. Some of the phosphorylation sites are located within the microtubule binding domains of tau, and it has been shown that an increase of tau phosphorylation negatively regulates the binding of microtubules. In this context, it is noteworthy that, for example, Ser262 and Ser396, which lie within or adjacent to microtubule binding motifs, are phosphorylated in fetal tau and are hyperphosphorylated in the tau proteins of the abnormal paired helical filaments (PHFs) which form the neurofibrillary tangles (NFTs) present in the brains of AD patients. Paired helical filaments are ultrastructural components of neurofibrillary tangles (NFTs). PHFs are filamentous aggregates of tau proteins which are abnormally hyperphosphorylated and can be stained with specific anti-tau antibodies and detected by light microscopy. The same holds true for so called straight tau filaments. PHFs form twisted ribbons consisting of two filaments twisted around one another with a periodicity of about 80 nm. These pathological features are commonly referred to as "tau-pathology" or "tau-related pathology". For a more detailed description of neuropathological features of tauopathies refer to Lee et al., *Annu Rev Neurosci* 2001, 24: 1121 and Götz J, *Brain Res Brain Res Rev* 2001, 35: 266. In addition to Alzheimer's disease (AD), NFTs are abundant in several other neurodegenerative diseases, including frontotemporal dementia with Parkinsonism linked to chromosome 17 (FTDP-17), caused by mutations in the tau gene (Hutton et al., *Nature* 1998, 393: 702; Poorkaj et al., *Ann Neurol* 1998, 43: 815; Spillantini et al., *Proc Natl Acad Sci USA* 1998, 95: 7737).

Besides NFTs, β-amyloid is the principal histopathological hallmark of AD. β-amyloid consists of hydrophobic Aβ peptides which have a strong tendency to aggregate into various oligomeric and filamentous states. SDS-stable oligomers and protofibrils appear to be particularly neurotoxic (Hartley et al., *J Neurosci* 1999, 19:8876-8884). Frautschy and coworkers investigated the significance of extracellular β-amyloid deposits and their impact on AD pathology by injecting amyloid cores into rat brain (Frautschy et al., *Proc Natl Acad Sci USA* 1991, 88: 8362). The authors reported neurotoxic effects of amyloid and observed a microglial inflammatory response and neuronal loss, but no tau-related pathology such as abnormal tau aggregation was observed. An induction of microtubule-associated tau phosphorylation at the AT8 and 12E8/Ab31 epitopes was observed after injection of $A\beta_{42}$ into brains of aged rhesus monkeys but not after injection into rat brains (Geula et al., *Nat Med* 1998, 4: 827).

β-amyloid plaques and neurofibrillary tangles (NFTs) are the defining neuropathological hallmarks of Alzheimer's disease, but their pathophysiological relation was up to now unclear. Previous attempts in generating animal model systems for the formation of fibrillar aggregates of tau and neurofibrillary tangles were without success in respect to the formation of aggregates and tangles with characteristic features observed in human disease. Likewise, transgenic mouse models based on mutations in the amyloid precursor protein exhibit only partial AD-like pathology. Such animals develop amyloid plaques, which are immunoreactive for hyperphosphorylated tau, resembling those in AD diseased brains, but lack any neurofibrillary or tangle-like features (Sturchler-Pierrat et al., *Proc Natl Acad Sci USA* 1997, 94: 13287). These APP animal models are subject to patent applications claiming their use for testing therapeutic agents for the treatment of neurodegenerative diseases (Sommer and Staufenbiel, patent application WO 9803644). Another patent application (Hutton et al., WO 9957129) describes a transgenic animal model expressing a tau polypeptide. The tau gene sequences used for generating those transgenic animals carry mutations which are linked to tau pathologies in humans. However, a significant number of neurofibrillary tangles, or any neurofibrillary tangles at all, were not observed. Thus, this animal model seems to be of only limited use as a model for a disease with pathologic features related to NFT formation, such as AD. Although recently it has been reported that transgenic mice expressing pathogenic human tau mutations form abnormal tau-containing filaments in brains (Lewis et al., *Nat Genet* 2000, 25:402; Götz et al., *J Biol Chem* 2001, 276:529), and that these filaments display similarities with neurofibrillary tangles (NFTs) of several human neurodegenerative diseases including Alzheimer's disease (AD) and frontotemporal dementia with parkinsonism linked to chromosome 17 (FTDP-17), their numbers are considerably lower than the ones commonly found in human diseases (Götz, *Brain Res Brain Res Rev* 2001, 35:266). This quantitative limitation precludes the use of these transgenic mice as a model system for said diseases. Thus, there is an urgent need for a suitable animal model system for the formation of genuine NFTs.

Now, with respect to the present invention, it is possible to generate an animal model system, characterized by an accelerated production and an increased number of NFTs as well as by specific features of NFTs which are similar to those seen in human AD patients. Therefore, it is an object of the present invention to provide a non-human animal model and an in-vivo assay system useful for testing of therapies, compounds and modulating agents of neurodegenerative diseases associated with the formation of neurofibrillary tangles, in particular Alzheimer's disease. The present invention shows that injection of β-amyloid $A\beta_{42}$ fibrils into brains of P301L mutant tau transgenic mice cause a several-fold increase in the numbers of NFTs in cell bodies within the amygdala from where neurons project to the injection sites. Another feature of the present invention is the accelerated production of NFTs.

The singular forms "a", "an", and "the" as used herein and in the claims include plural reference unless the context dictates otherwise. For example, "an animal" means as well a plurality of animals, and so forth. The term "fragment" as used herein is meant to comprise e.g. an alternatively spliced, or truncated, or otherwise cleaved transcription product or translation product. The term "derivative" as used herein refers to a mutant, or an RNA-edited, or a chemically modified, or otherwise altered transcription product, or to a mutant, or chemically modified, or otherwise altered translation product. For instance, a "derivative" may be generated by processes such as altered phosphorylation, or glycosylation, or, acetylation, or lipidation, or by altered signal peptide cleavage or other types of maturation cleavage. These processes may occur post-translationally. The term "variant" as used herein refers to any polypeptide or protein, in reference to polypeptides and proteins disclosed in the present invention, in which one or more amino acids are added and/or substituted and/or deleted and/or inserted at the N-terminus, and/or the C-terminus, and/or within the native amino acid sequences of the native polypeptides or proteins of the present invention. Furthermore, the term "variant" shall include any shorter or longer version of a polypeptide or protein. Variants comprise proteins and polypeptides which can be isolated from nature or be produced by recombinant and/or synthetic means. Native proteins or polypeptides refer to naturally occurring truncated or secreted forms, naturally occurring variant forms (e.g. splice-variants) and naturally occurring allelic variants. The terms "agent", "modulating agent", or "compound" refer to any substance, chemical, composition or extract that have a positive or negative biological effect on an animal, a cell, tissue, body fluid, or within the context of any biological system, or any assay system examined. They can be agonists, antagonists, partial agonists or inverse agonists of a target. Such agents, modulating agents, or compounds may be nucleic acids, natural or synthetic peptides or protein complexes, or fusion proteins. They may also be antibodies, organic or anorganic molecules or compositions, small molecules, drugs and any combinations of any of said agents above. They may be used for testing, for diagnostic or for therapeutic purposes.

Neurodegenerative diseases or disorders according to the present invention comprise Alzheimer's disease, Pick's disease, fronto-temporal dementia with parkinsonism (FTDP-17), progressive nuclear palsy, corticobasal degeneration, parkinsonism-dementia complex of Guam, and other tauopathies. Further conditions involving neurodegenerative processes are, for instance, Parkinson's disease, Huntington's disease, amyotrophic lateral sclerosis and other motor neuron diseases, cerebro-vascular dementia, multiple system atrophy, and mild cognitive impairment. A list of tau-related diseases and disorders can be found in a publication by Lee et al. (*Annu Rev Neurosci,* 2001, 24:1122).

The present invention features a method of increasing the number of neurofibrillary tangles in a non-human transgenic animal which expresses a recombinant gene coding for tau protein wherein the increase of neurofibrillary tangles is induced through admission of APP or a fragment, or derivative, or variant thereof, in particular β-amyloid. In another aspect the present invention features a method of accelerating the production of neurofibrillary tangles in a non-human transgenic animal which expresses a recombinant gene coding for tau protein wherein the accelerated production of neurofibrillary tangles is induced through admission of APP or a fragment, or derivative, or variant thereof, in particular β-amyloid.

In a preferred embodiment of the featured methods said admitted β-amyloid is $A\beta_{42}$. It is further preferred that the admitted $A\beta_{42}$ is fibrillar, pre-aggregated, or aggregated.

The non-human transgenic animal is preferably a mammal, in particular a rodent such as a mouse, a guinea pig, or a rat. According to the instant invention, the transgenic animal in which neurofibrillary tangles are to be produced is preferably a mouse. In a preferred embodiment, said transgenic mouse expresses a recombinant gene coding for human tau, preferably the tau protein isoform containing four microtubule binding motifs, also referred to as the four-repeat isoform. In another preferred embodiment, said transgenic mouse expresses a recombinant gene coding for P301L mutant tau. However, other tau gene sequences having a mutation linked to tau pathology may also be expressed as a trans-gene in said animal.

In a preferred embodiment of the present inventive methods, β-amyloid is admitted, or administered, through injection into the brain of said animal, in particular through injection into the hippocampus or the cortex. A preferred method of admission, or administration, is by stereotaxic injection (Paxinos, *The Mouse Brain in Stereotaxic Coordinates*, Academic Press, San Diego, 1997). However, admission, or administration, of β-amyloid shall not be limited to injection into the brain of said animal. Other means of administration of β-amyloid can be, for instance, orally, nasally, systemically, or subcutaneously.

In another preferred embodiment of the instant invention, β-amyloid or another fragment, or derivative, or variant of APP is admitted through co-expressing a recombinant gene coding for APP, said APP being enzymatically processed to generate a cleavage product, said cleavage product being preferably β-amyloid. Preferentially, said co-expressed APP is a mutant APP, particularly a mutant associated with Alzheimer's disease pathology. The co-expression can be accomplished, for instance, by recombinant expression methods, including direct gene-transfer techniques such as mechanical microinjection of recombinant gene sequences coding for APP, as well as indirect techniques employing biological vectors such as recombinant vectors, especially recombinant viruses such as retroviruses or adenoviruses. These methods are known to a person skilled in the art and are described in detail (e.g. Behr, *Acc Chem Res* 1993, 26:274; Mulligan, *Science* 1993, 260:926; Wolff, *Curr Opin Neurobiol* 1993, 3:743). Co-expression of a recombinant gene coding for APP can also be accomplished transgenically, for instance by crossing transgenic animals expressing a recombinant tau gene with animals expressing a recombinant gene coding for APP, to generate bigenic or double-transgenic animals.

Strategies and techniques for the generation and construction of such animals are known to those of skill in the art (see e.g. Capecchi, *Science* 1989, 244:1288-1292 and Hogan et al., 1994, *Manipulating the Mouse Embryo: A Laboratory Manual*, Cold Spring Harbor Laboratory Press, Cold Spring Harbor, N.Y.).

In one preferred embodiment of the present inventive methods, the increase and/or the accelerated production of neurofibrillary tangles is predominantly in the amygdala of the animal's brain, in particular the basolateral amygdala. However, such an increase and/or accelerated production of neurofibrillary tangles shall not be limited to the amygdala. Other regions of the brain, for instance, the parietal cortex, are also capable of displaying the desired effect. It is preferred that the increase of neurofibrillary tangles is several-fold, preferably at least two-fold, as compared to a control animal to which no APP or a fragment, or derivative, or variant thereof, in particular β-amyloid, has been administered. A proper control animal, for instance, can be an animal which has been sham-injected, or mock-injected, or control-injected, for instance with an Aβ$_{42-1}$ reverse peptide. In another preferred example, the increase of neurofibrillary tangles is at least five-fold as compared to a control animal to which no APP or a fragment thereof, in particular β-amyloid, has been administered.

The herein described methods can further be useful for the induction of other neuropathological features similar to the features observed in Alzheimer's disease, such as the formation of neuropil threads and/or the degeneration of neurites.

The invention features a non-human transgenic animal which expresses a recombinant gene coding for tau protein wherein said animal is capable of producing neurofibrillary tangles. Furthermore, a feature of the present invention is a non-human transgenic animal which expresses a recombinant gene coding for tau protein wherein said animal is capable of producing an increased number of neurofibrillary tangles. Additionally, another feature of the invention is a non-human transgenic animal which expresses a recombinant gene coding for tau protein wherein said animal is capable of an accelerated production of neurofibrillary tangles.

It is one particular embodiment of the invention that all of the above featured non-human transgenic animals produce neurofibrillary tangles which are comparable to those commonly found in human neurodegenerative diseases.

In a preferred embodiment, the herein described animals comprise APP or a fragment, or derivative, or variant thereof, in particular β-amyloid, in an amount sufficient to induce the production of neurofibrillary tangles.

In a preferred embodiment, the instant invention claims a non-human transgenic animal which expresses a recombinant gene coding for tau protein wherein the increase in the number of neurofibrillary tangles and/or the accelerated production of neurofibrillary tangles is induced through admission of APP or a fragment, or derivative, or variant thereof, in particular β-amyloid. The admission, or administration, of β-amyloid is preferably accomplished through injection into the brain of said animal, in particular through injection into the hippocampus or the cortex. Alternatively, said admission can be accomplished through co-expressing a recombinant gene coding for APP or a fragment, or derivative, or variant thereof, said APP being enzymatically processed to generate a cleavage product, said cleavage product being preferably β-amyloid. Preferentially, said co-expressed APP is a mutant APP, particularly a mutant associated with Alzheimer's disease pathology. The co-expression can be carried out, for instance, by recombinant expression methods as described in the instant invention.

The transgenic animals according to the present invention provide an in-vivo assay to determine or validate the efficacy of therapies, or modulatory agents, or compounds for the treatment of neurodegenerative diseases, in particular Alzheimer's disease, frontotemporal dementia (FTD), and other neurodegenerative diseases accompanied by neurofibrillary tangle formation. In a preferred embodiment of the present invention, said in-vivo assay is useful for determining or validating the efficacy of amyloid-lowering therapies, such as β-amyloid vaccination, or NFT-reducing therapies.

According to the present invention, an in-vivo assay comprises, for instance, the following steps: (i) providing a non-human transgenic animal which produces neurofibrillary tangles, said animal being generated by the methods of the instant invention, (ii) contacting said animal with a compound or modulatory agent, or alternatively, applying a therapy in said animal, and (iii) assessing the ability of said compound or modulatory agent, or said therapy to modulate the formation of neurofibrillary tangles, and/or the formation of neuropil threads, and/or the degeneration of neurites, or other AD-related pathology in said animal. Determining the formation of neurofibrillary tangles in said in-vivo assay can be accomplished by a variety of methods, for instance immunohistochemistry and electron microscopy, and it can comprise the utilization of conformation-dependent antibodies that are capable of recognizing and discriminating a tau molecule in the context of neurofibrillary tangles from tau molecules existing in other states of aggregation. In a preferred embodiment, said conformation-dependent antibodies are optically labeled, preferably flourescently labeled, and can be detected, for instance, by a number of optical methodologies such as fluorescence polarisation spectroscopy, fluorescence correlation spectroscopy, fluorescence cross-correlation spectroscopy, fluorescence intensity distribution analysis, fluorescence lifetime measurements, fluorescence anisotropy measurements, fluorescence resonance energy transfer, or combinations thereof. Alternatively, in another embodiment, antibodies that are capable of recognizing phosphorylated epitopes of tau, in particular epitopes whose degree of phosphorylation correlates with the state of tau aggregation and neurofibrillary tangle formation as observed in Alzheimer's disease, in particular the tau epitope S422, can be used.

Other features and advantages of the invention will be apparent from the following detailed description of the figures and examples, which are illustrative only and not intended to limit the remainder of the disclosure or the scope of the invention in the claims.

FIG. 1

Stereotaxic injections of suspensions of $A\beta_{42}$ fibrils or $A\beta_{42-1}$ into the somatosensory cortex of one hemisphere, as well as the CA1 region of the hippocampus of the contralateral hemisphere of mouse brains. Sites of injections are indicated with symbolic syringes.

FIG. 2

Stereotaxic injections of $A\beta_{42}$ or $A\beta_{42-1}$ fibrils into the somatosensory cortex and the CA1 region of the hippocampus of mouse brains. Electron microscopy confirmed that aggregated synthetic $A\beta_{42}$ formed fibrils (A), whereas a reverse control peptide, $A\beta_{42-1}$ (B), did not. Mice brains were analyzed 18-60 day post-injection. Scale bars: A,B: 0.4 µm.

FIG. 3

Suspensions of $A\beta_{42}$ fibrils or $A\beta_{42-1}$ were injected stereotaxically into the somatosensory cortex of one hemisphere, as well as the CA1 region of the hippocampus of the contralateral hemisphere of mouse brains. Antibody 6E10 revealed that $A\beta_{42}$ fibrils were present at the injection sites at least for 45 days following the injection (A). As staining controls, amyloid plaque-containing $APP^{sw}$ transgenic (Hsiao et al., *Neuron* 1995, 15: 1203) and human AD brain sections were included. $A\beta_{42}$ and $A\beta_{42-1}$ increased the occurrence of reactive astrocytes both around the injection site (B), and in the amygdala (C). Reactive astrocytosis persisted for at least 45 days. Stereotaxic application of Texas red-coupled dextran into identical coordinates stained a subset of neurons in the amygdala confirming that these projected to the injection sites (D). A-D: Seven month-old P301L female analyzed 45 days after injection. Scale bars: A-D: 50 µm.

FIG. 4

Presence of neurofibrillary tangles (NFTs) in P301L tau transgenic mice induced by $A\beta_{42}$ fibrils. $A\beta_{42}$ fibrils induced the Gallyas-positive formation of numerous NFTs and neuropil threads in the amygdala and, occasionally, the cortex as early as 18 days following the injection. Amygdala of a six month-old female P301L transgenic mouse analyzed 18 days post injection. Scale bar: 25 µm.

FIG. 5

$A\beta_{42}$ fibrils trigger the formation of numerous Gallyas-positive NFTs and neuropil threads in the amygdala and, occasionally, the cortex of P301L transgenic mice as early as 18 days following the injection. Gallyas silver impreganations of NFTs in the amygdala and parietal cortex of $A\beta_{42}$-(A,C) and $A\beta_{42-1}$-injected (B) P301L tau transgenic mice. A subset of NFTs was also stained by thioflavin-S (D). A: Eight month-old P301L male analyzed 40 days post injection; B: 6.5 month-old P301L female analyzed 40 days post injection; C: Six month-old female P301L transgenic mouse analyzed 18 days post injection D: Seven month-old P301L female analyzed 45 days post injection. Scale bars: A,B: 25 µm; C,D: 12.5 µm

FIG. 6

Neurofibrillary tangles (NFTs) in P301L tau transgenic mice induced by $A\beta_{42}$ fibrils. $A\beta_{42}$ fibrils trigger the formation of numerous Gallyas-positive NFTs and neuropil threads in the amygdala and, occasionally, the cortex of P301L transgenic mice (A). The induced NFTs were very similar to those found in brains obtained from AD patients (B). Both slides were stained in parallel by the same protocol. A: 5.25 month-old P301L male analyzed 21 days post injection. B: Human 86 year-old female AD patient.

FIG. 7

$A\beta_{42}$ fibrils trigger the formation of neurofibrillary tangles (NFTs) in P301L tau transgenic mice. Immuno-electron microscopy of thin sections of the amygdala reveals AD-like tau filaments (using antibody AT8). Scale bars:: low magnification view: 800 µm (A); high magnification view: 100 µm (B).

FIG. 8

Gallyas-positive NFTs in the amygdala. NFTs were counted on day 22 post-injection in $A\beta_{42}$-, $A\beta_{42-1}$-, and uninjected P301L transgenic mice, non-transgenic litter mate controls as well as transgenic mice expressing wild-type human tau (Probst et al., *Acta Neuropathol (Berl)* 2000, 99: 469). The mean age in months ±SD at the time of analyses is indicated. Gallyas-positive NFTs were counted according to the herein described methods and represent the sum in 20 standardized frontal sections comprising both the ipsilateral and the contralateral amygdala. Mann-Whitney U-test: P=0.007 (2-tailed exact significance) comparing $A\beta_{42}$- with $A\beta_{42-1}$-injected P301L mice.

FIG. 9

Abnormal phospho-epitopes of tau induced by $A\beta_{42}$ fibrils. The R145d epitope S422 was not phosphorylated in the hippocampus and cortex (A), but specifically induced by $A\beta_{42}$ fibrils in the amygdala (B), high magnification view). In contrast to R145d and AT100, the AT8 epitope was phosphorylated in many neurons of the hippocampus, cortex (C) and amygdala (D, high magnification view). A-D: Six month-old P301L male analyzed 18 days post injection. Scale bars: A,C: 100 µm; B,D: 25 µm. Schematic map of a mouse brain hemisphere indicating relevant brain regions (E).

FIG. 10

Abnormal phospho-epitopes of tau induced by $A\beta_{42}$ fibrils. Double immuno-fluorescence staining with R145d (tau phospho-epitope S422) and AT100 (phospho-epitope S212/T214) revealed that R145d-positive neurons in the amygdala were AT100-positive (A, B, merge: C). Scale bar: 40 µm.

FIG. 11

Abnormal phospho-epitopes of tau induced by $A\beta_{42}$ fibrils. Approximately half of the R145d-positive neurons (A,B) beared Gallyas-positive neurofibrillary tangles (C,D), and generally these included the neurons that were most intensely stained by R145d (phospho-S422) (indicated by arrows). A-D: Seven month-old P301L female analyzed 45 days post injection. Scale bars: 40 µm.

EXAMPLES

Figure 1:
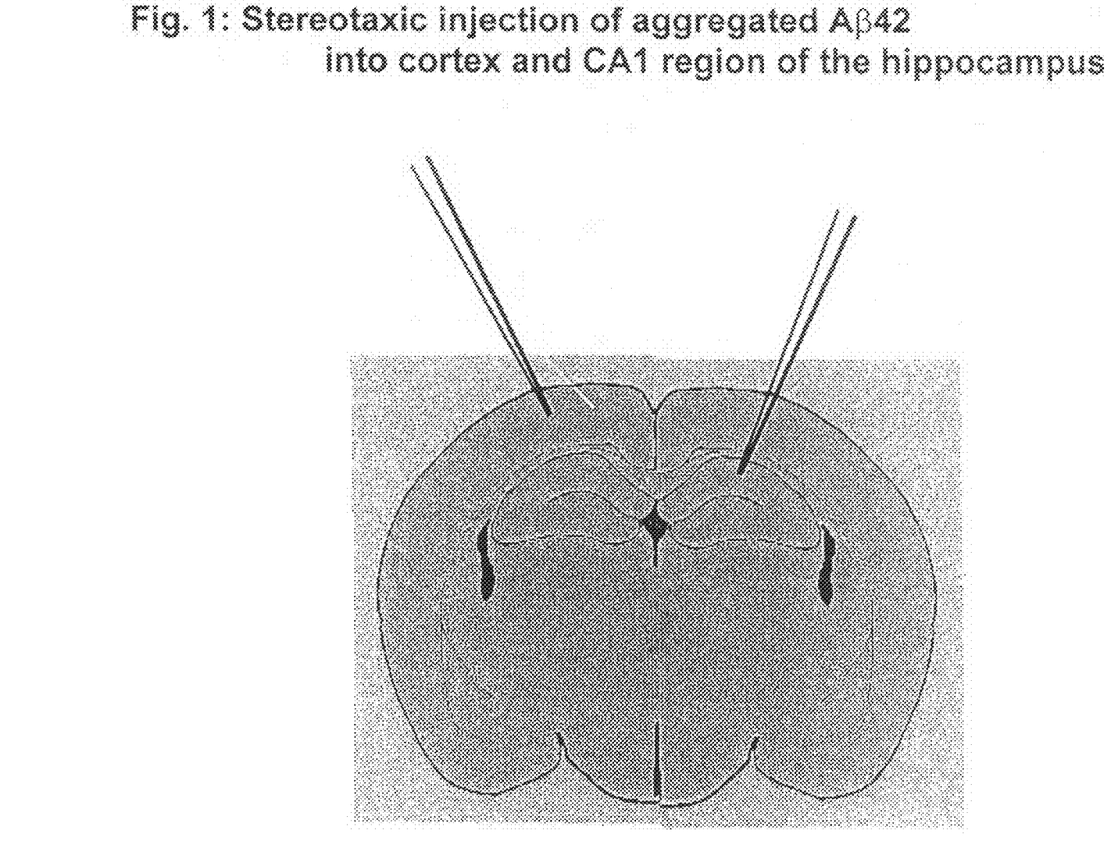
Figure 2:
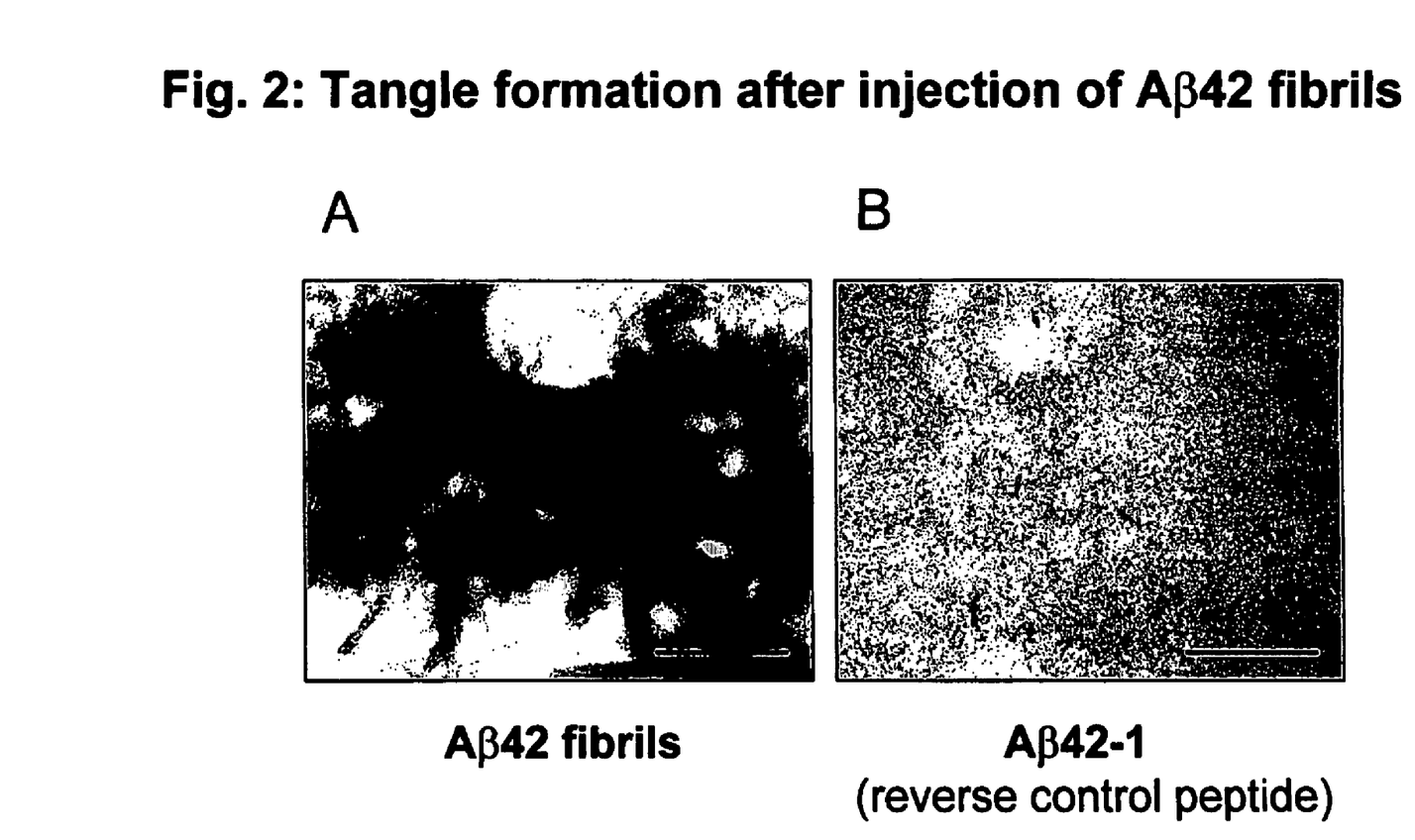
Figure 3:
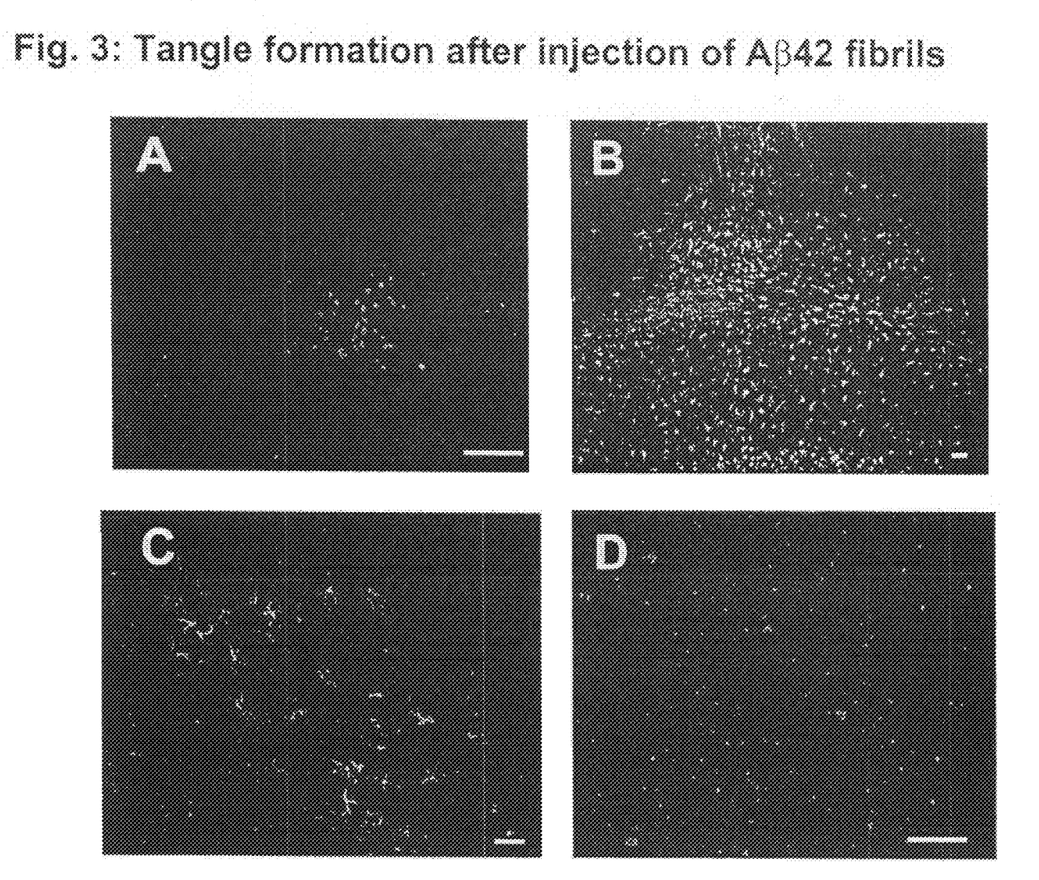

To determine whether β-amyloid can accelerate NFT formation, synthetic $A\beta_{42}$ fibrils were injected into the somatosensory cortex and the hippocampus of five to six month-old P301L tau transgenic mice and non-transgenic littermates, (refer to methods section (i)-(iii)). As a control peptide, the reversed sequence, $A\beta_{42-1}$, derived from the identical source was used (methods section (ii)). $A\beta_{42}$ fibrils were generated by shaking incubation at 37° C. and were confirmed by electron microscopy (FIG. 2A,B) (methods section (ii) and (iii)). $A\beta_{42}$ fibrils were stable in vivo in both P301L transgenic and wild-type control mice and were readily detectable at least until 45 days following the injections (FIG. 3A). Brain amyloid deposits were accompanied by significant reactive astrogliosis at both the injection sites (FIG. 3B)

and the amygdala (FIG. 3C) (for methods refer to section (iv)); these deposits were observed in both $A\beta_{42}$- and in control-injected transgenic mice and persisted for at least 45 days post-injection. This reaction may be related to the fact that neurons in the amygdala project to the injection sites, as shown by retrograde transport of Texas red-conjugated dextran from the injection site in the somatosensory cortex to cell bodies in the amygdala (FIG. 3D) (methods section (iv)).

Figure 4:
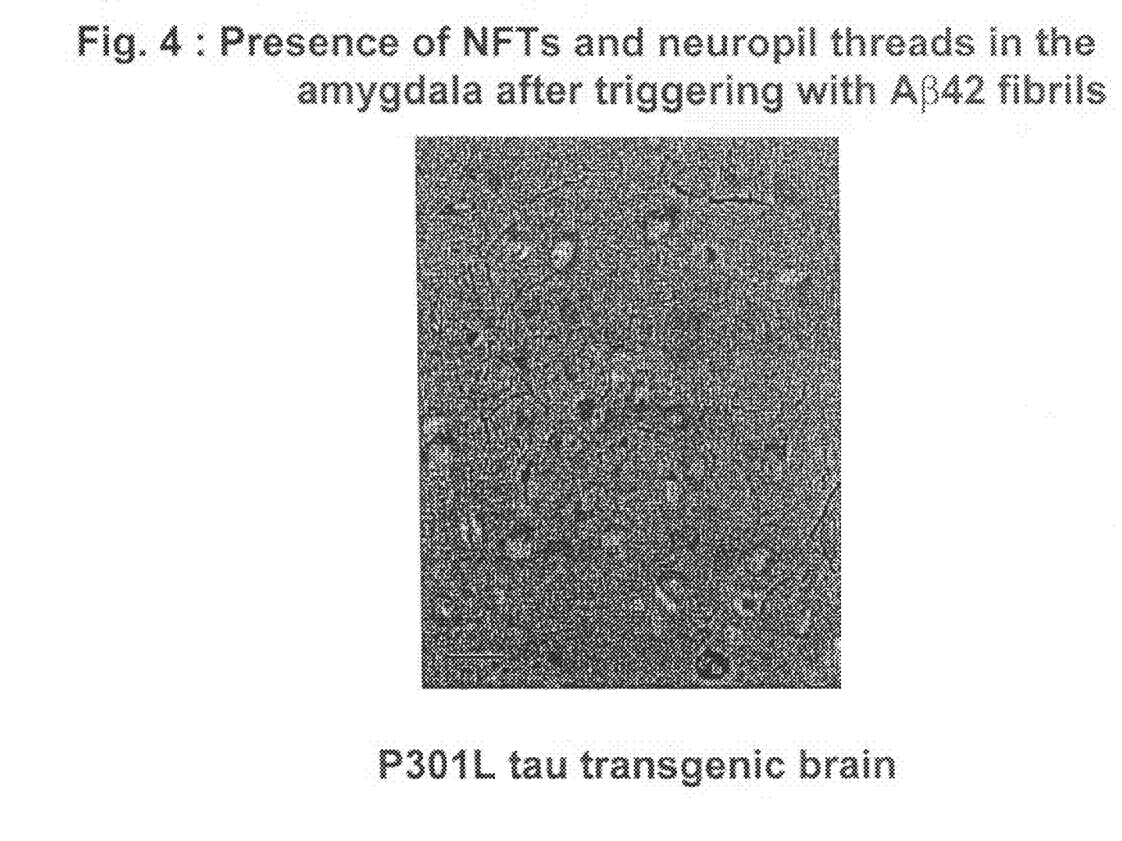
Figure 5:
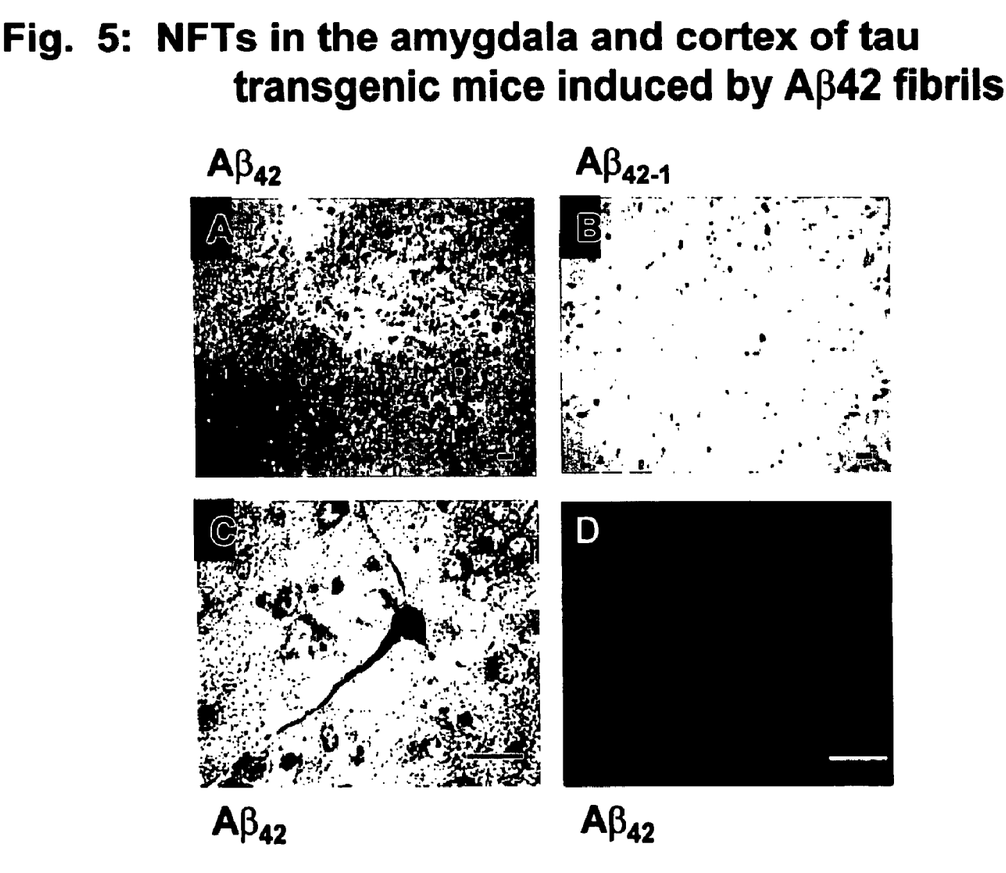
Figure 6:
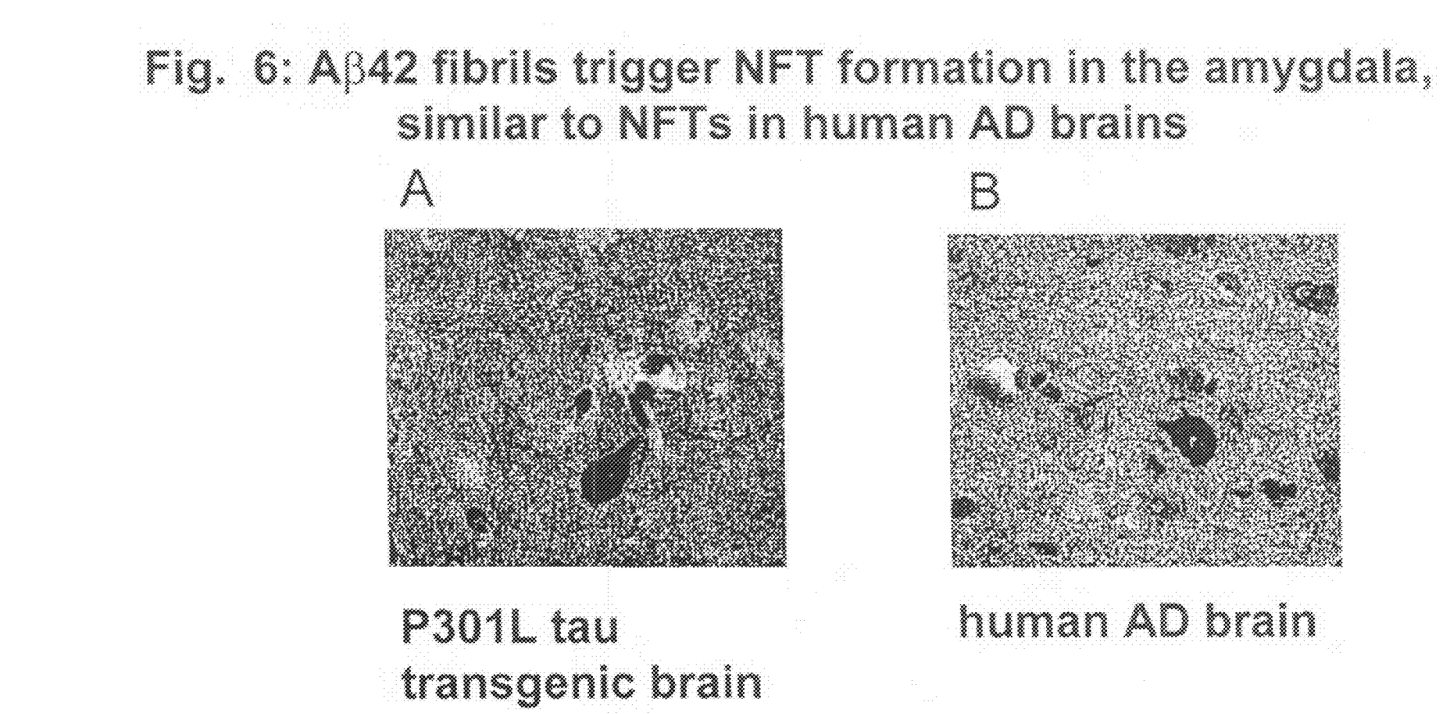
Figure 7:
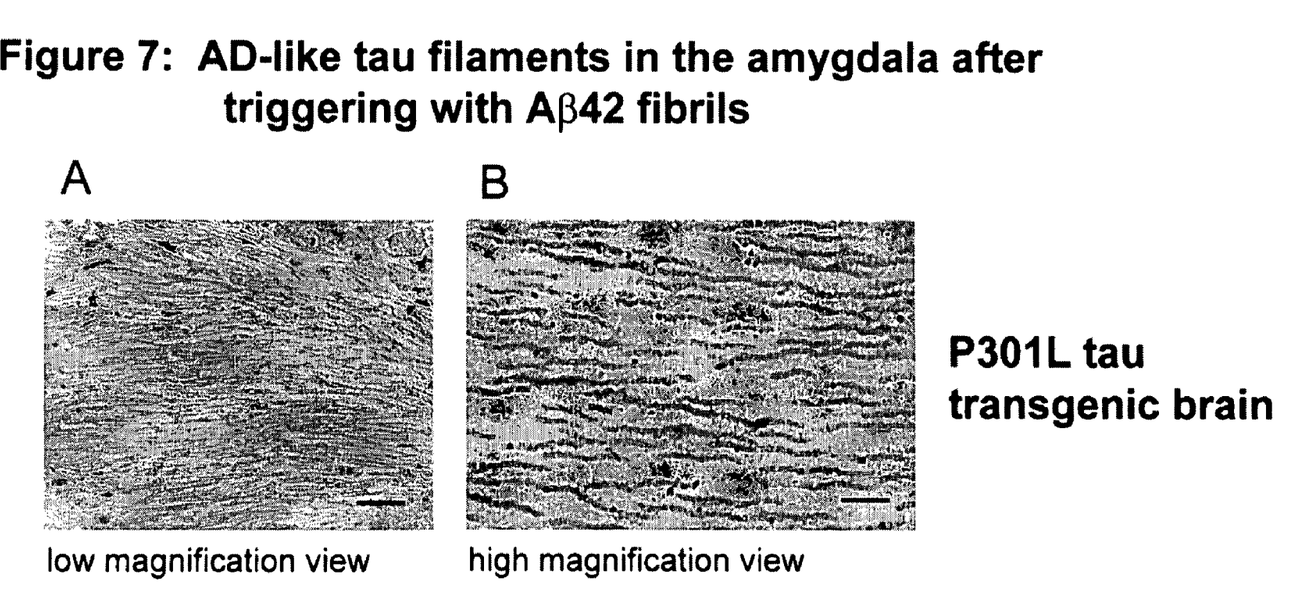

Eighteen days following the injections of $A\beta_{42}$, Gallyas silver impregnation (section (iv)) revealed numerous NFTs (FIG. 5A-C, FIG. 6A), along with neuropil threads and degenerating neurites (FIG. 4) in the amygdala of P301L, but not wild-type mice. Occasional NFTs were also present in the parietal cortex (FIG. 5C). The NFTs in mice (FIG. 6A) were very similar to those in AD brains stained in parallel by the same protocol (FIG. 6B). Moreover, the neuropil threads were similar to those known in AD (Braak et al., *Neurosci Lett* 1986, 65: 351; McKee et al., *Ann Neurol* 1989, 26: 652; Velasco et al., *Brain Res* 1998, 813: 329). A subset of Gallyas-positive neurofibrillary tangles in the mice were also stained with thioflavin-S, consistent with the histopathology of AD (FIG. 5D). The filaments had a width of 20-25 nm and a periodicity of 90 nm, and are best described as twisted ribbons (FIG. 7). In human carriers, the P301L mutation causes predominant expression of 4 repeat (4R) isoforms, with a small amount of wild-type 3R isoforms, resulting in 15 nm wide twisted filaments with a periodicity of greater than 130 nm (Spillantini et al., *Am J Pathol* 1998, 153: 1359). Because mice endogenously express only 4R tau isoforms, and the transgene was designed to express 4R human P301L tau, the filaments observed here contained no 3R tau. Importantly, the human intronic FTDP-17 mutations that reduce the formation of 3R tau also cause twisted ribbons mainly composed of 4R tau. It is therefore possible that the relative amounts of 3R and 4R isoforms contribute to the ultrastructural morphology of the filaments.

Figure 8:
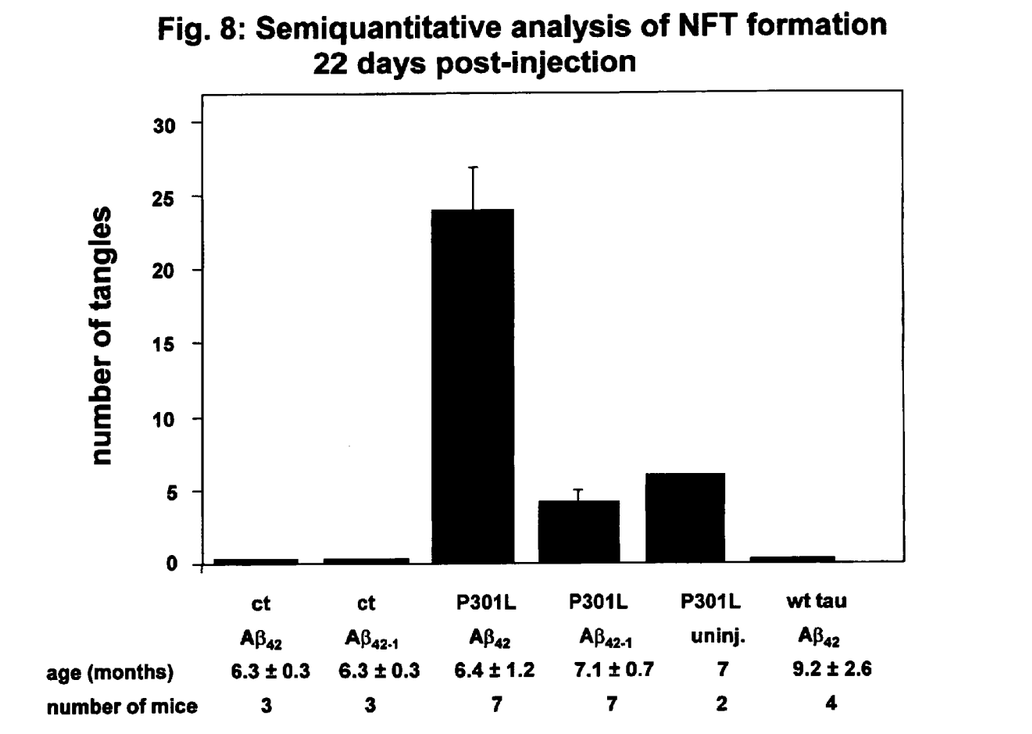

Quantitative analyses revealed five times more Gallyas-positive NFTs in the $A\beta_{42}$-injected P301L mice as compared to $A\beta_{42\text{-}1}$- or uninjected P301L mice (FIGS. 5A,B; FIG. 8). Cross-sectional time-course analyses of NFT formation showed initial NFTs 18 days after $A\beta_{42}$ injection, with further increases in numbers (n=58) at least until 60 days following the injection. NFT formation in both hemispheres in the $A\beta_{42}$-injected P301L mice did not vary with gender (females: 23±21; males: 23±4; n=7, P=0.86, Mann-Whitney U-test). In contrast, $A\beta_{42\text{-}1}$-injected P301L males developed few NFTs and P301L females no NFTs, at 6 to 8.5 months of age. This difference was statistically significant (females: 0; males: 5.8±1.9; n=7, P<0.01, Mann-Whitney U-test). The presence of the tau mutation is preferred for inducing NFT formation.

A surprising and remarkable finding was the spatial separation of the site of $A\beta_{42}$ injection and remote NFT formation in the amygdala, with no significant differences between the ipsilateral and the contralateral amygdala (11.4±10.13 and 9.4±8.0; n=7, P=0.058, Wilcoxon Signed Ranks Test). This suggests the possibility that damage to presynaptic terminals or axons of neurons that project to the injection site caused NFT formation in the respective cell bodies. The anatomical separation of amyloid deposition and NFT formation is therefore consistent with $A\beta_{42}$-induced axonal damage, and, possibly, impaired axonal transport of tau (Varadarajan et al., *J Struct Biol* 2000, 130: 184). We confirmed that the affected neuronal population in the amygdala projected to the cortical injection sites by showing retrograde transport of Texas red-conjugated dextran from the injection sites to the amygdala (FIG. 3D). Other mechanisms of somatodendritic accumulation of tau are less likely: First, we excluded a direct exposure to $A\beta_{42}$ fibrils of the cell bodies in the amygdala by immunohistochemistry. Second, increases in synthesis of tau protein levels are unlikely as indicated by the absence of axonal dilatations or spheroids in amygdala neurons. Third, a diffusible toxic factor would hardly explain the failure of neurons adjacent to the injection sites to develop NFTs. In human patients with AD, an anatomical separation of amyloid plaques and NFTs is frequently found; with amyloid deposits around synapses and NFTs in the respective cell bodies of projection neurons (Price and Sisodia, *Ann Rev Med* 1994, 45: 435). In addition, the amygdala is among the most vulnerable areas affected early by NFT formation in human patients (Arnold et al., *Cereb Cortex* 1991, 1: 103). High vulnerability of the amygdala in our P301L mice is supported by the fact that neurons in the amygdala expressed similar levels of the transgene as compared to cortical or hippocampal pyramidal neurons, yet these developed hardly any NFTs (Götz et al., *J Biol Chem* 2001, 276: 529). Although our experiments did not formally address the involvement of astrocytes and microglia in NFT formation, activation of these cells alone clearly was not sufficient for NFT formation because $A\beta_{42}$ and $A\beta_{42\text{-}1}$ similarly activated astrocytes and microglial cells both around the injection sites and in the amygdala (FIGS. 3B,C).

The formation of NFTs in AD is associated with hyper-phosphorylation and conformational changes of tau (Grundke-lqbal et al., *Proc Natl Acad Sci USA* 1986, 83: 4913; Braak and Braak, *Neurobiol Aging* 1995, 16: 271; Jicha et al., *J Neurosci Res* 1997, 48: 128). To determine whether the $A\beta_{42}$-induced NFT formation in P301L mice was associated with altered phosphorylation and conformation of tau, we used antibodies directed against abnormal phospho-epitopes (R145d, pS$^{422}$, AT100, TG3) (Goedert et al., *Biochem J* 1994, 301: 871; Dickson et al., *Neurobiol Aging* 1995, 16: 285; Tanaka et al., *FEBS Lett* 1998, 426: 248), hyperphos-phorylated epitopes (AT8, S199P, AT180, 12E8, AD2, PHF1) (Goedert et al., *Biochem J* 1994, 301: 871; Greenberg et al., *J Biol Chem* 1992, 267: 564; Goedert et al., *Neurosci Lett* 1995, 189: 167; Seubert et al., *J Biol Chem* 1995, 270: 18917; Buee-Scherrer et al., *Brain Res Mol Brain Res* 1996, 39: 79; Delacourte et al., *Ann Neurol* 1998, 43, 193; Sergeant et al., *J Neurochem* 1999, 72: 1243), as well as conformation-dependent antibodies (TG3, MC1) (Jicha et al., *J Neurosci Res* 1997, 48: 128; Dickson et al., *Neurobiol Aging* 1995, 16: 285), by using standard published procedures (see methods section (iv) and Götz et al., *Proc Natl Acad Sci USA* 1998, 95: 12370).

Figure 9:
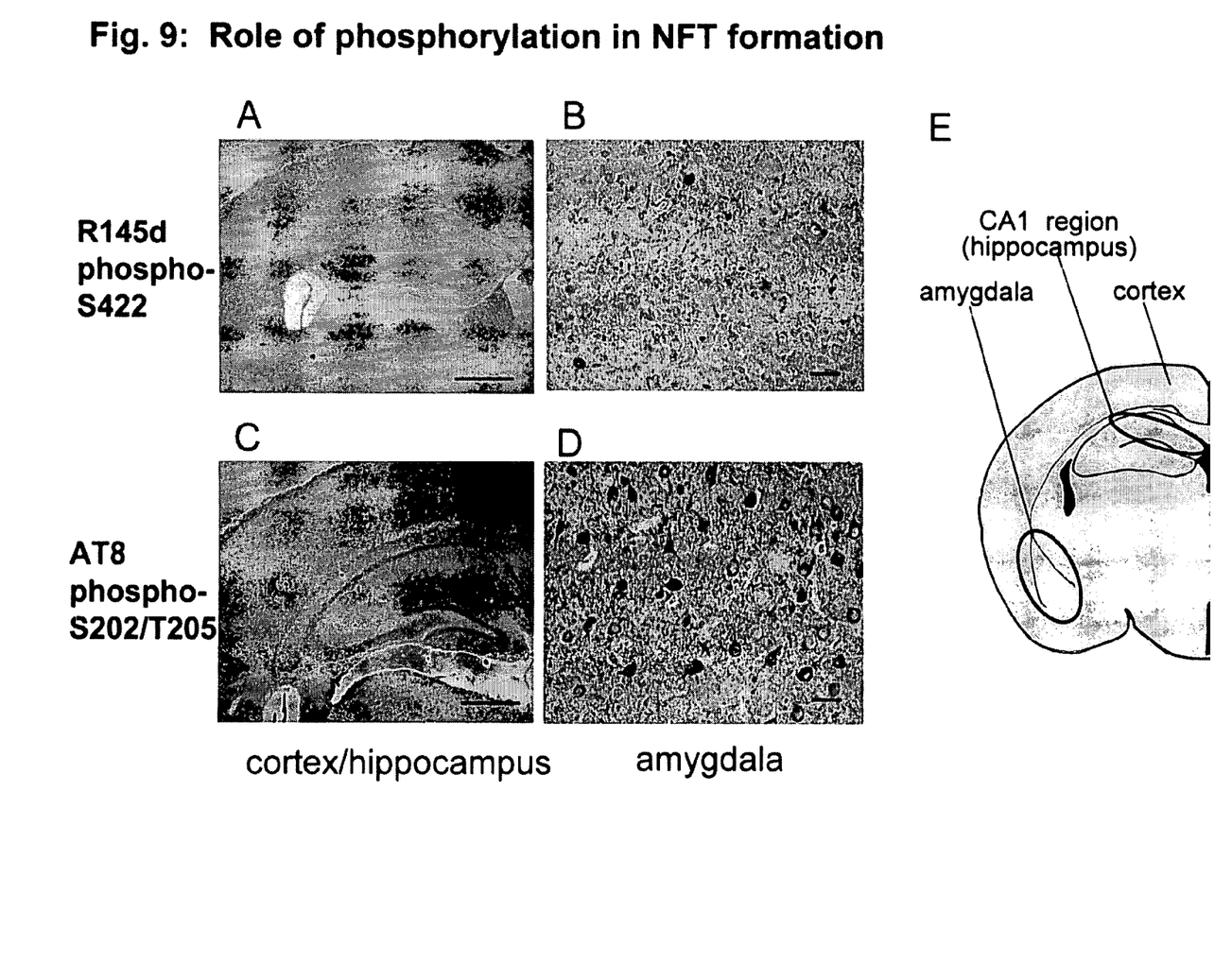
Figure 10:
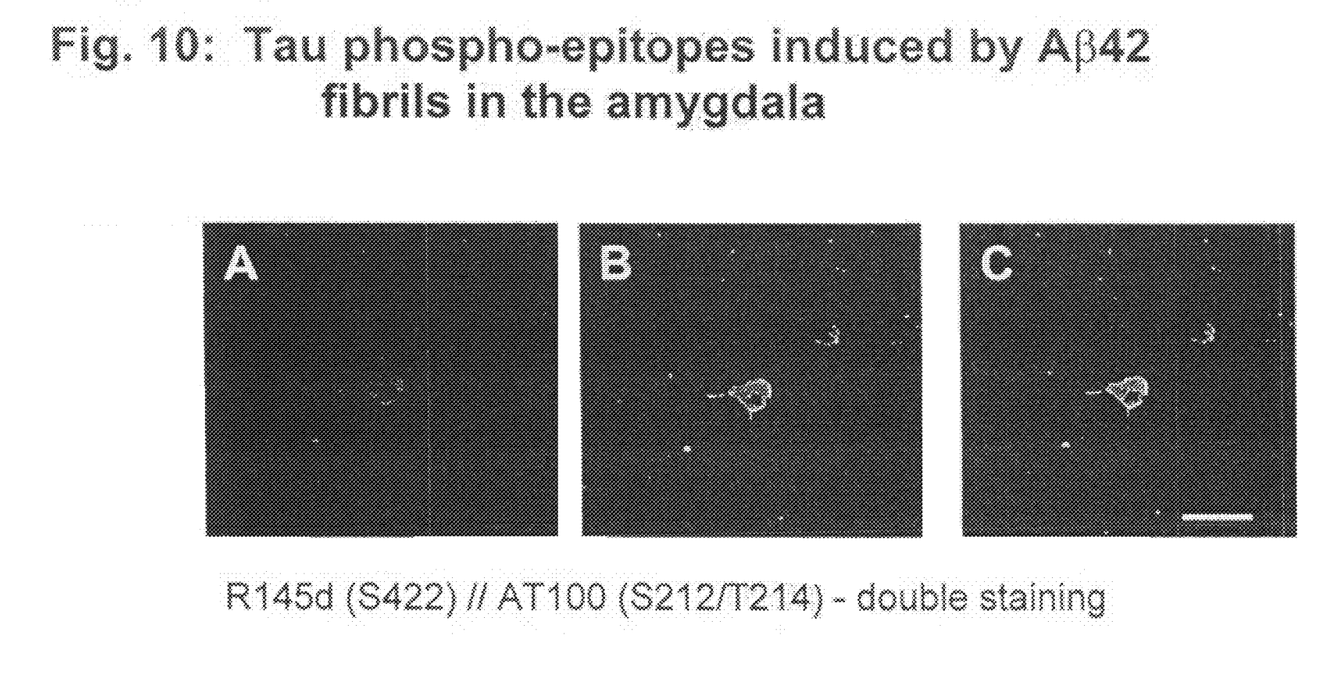
Figure 11:
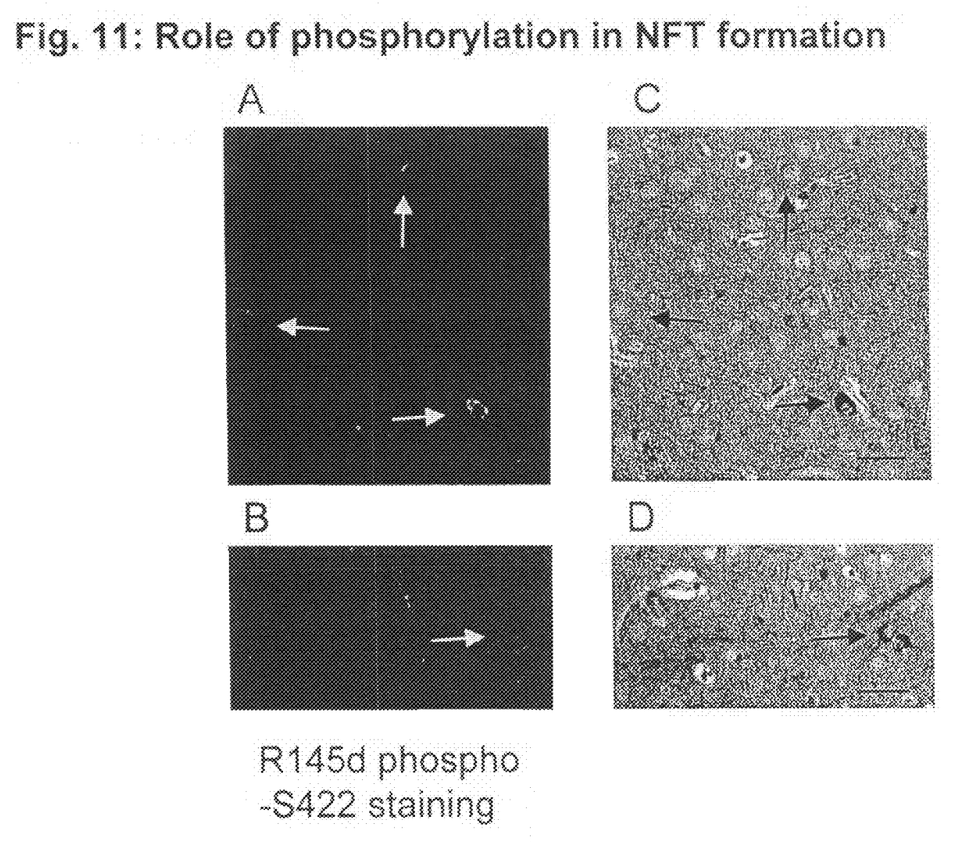

Whereas several antibodies, including AT8, detected phosphorylated tau throughout the brains of P301L mice independently of the injections, R145d/pS$^{422}$ and AT100 directed against phospho-epitopes S422 and S212/T214, respectively, specifically detected NFTs and neurons only in response to $A\beta_{42}$ (FIGS. 9A,B; FIG. 10A-C). Remarkably, the spatial distribution pattern of these abnormally phosphorylated forms of tau was identical to that observed by Gallyas stainings, and occurred, again, predominantly in the amygdala (FIGS. 9A,B). Co-staining revealed that neurons stained by R145d/pS$^{422}$ were also stained by AT100 (FIG. 10A-C). Neither R145d nor AT100 immunostained any cells in non-transgenic mice. The specificity of R145d, pS$^{422}$, and AT100 immunoreactivity for $A\beta_{42}$-associated abnormal phosphorylation was remarkable because these antisera revealed hardly any signals in uninjected or $A\beta_{42\text{-}1}$-injected P301L tau transgenic mice, and none in transgenic mice expressing wild-type human tau. Moreover, all Gallyas-positive NFTs were also stained by R145d, as indicated by sequential immunofluorescence and Gallyas silver impregnation protocols, strongly suggesting that the NFTs in P301L mice contained S422- phosphorylated tau. Semi-quantitative analyses revealed that approximately one half of the R145d-positive neurons (FIG. 11A,B) were Gallyas-positive (FIG. 11C,D), and R145d stained these neurons generally more intensely than cells without NFTs.

Together, the result of our immunostaining is consistent with the possibility that phosphorylation of epitopes S212/T214 and S422 is tightly associated with NFT formation. The herein disclosed data extend prior findings that $A\beta_{42}$ induced tau phosphorylation in vitro and in vivo at the AT8 and 12E8/Ab31 epitopes (Busciglio et al., Neuron 1995, 14: 879; Geula et al., Nat Med 1998, 4: 827). In our P301L mice, tau was phosphorylated at these epitopes, even in the absence of injected $A\beta_{42}$. Therefore, these epitopes may be necessary but clearly were not sufficient for NFT formation in P301L mice. By using R145d/$pS^{422}$ and AT100, we found that $A\beta_{42}$ injections were followed by phosphorylation of tau at S212/T214 and S422 suggesting a role of these epitopes in NFT formation.

In summary, the herein disclosed data establish that $A\beta_{42}$ fibrils can significantly accelerate NFT formation in P301L mice. The neurofibrillary tangles generated according to the inventive method closely resemble those extracted from brains of AD patients and the formation of which was achieved already within 18 days post-injection. The herein disclosed data demonstrate that, in transgenic mice, the interaction of β-amyloid with the P301L mutation was required for NFT formation—neither β-amyloid, nor the mutation alone, were sufficient to generate high numbers of NFTs. The mice generated according to the instant invention provide an in vivo assay to determine whether such amyloid-lowering therapies as Aβ vaccination are effective in preventing NFT formation in vivo.

Methods (i) Generation of transgenic mice: To generate transgenic mice, the human pathogenic tau mutation P301L was introduced into the cDNA encoding the longest human brain tau isoform by a PCR-mediated approach. This isoform contained exons 2 and 3 as well as four microtubule-binding repeats ($2^+3^+4R$, htau40). In order to be able to discriminate P301L tau transgenic from wild-type tau transgenic mice, a silent mutation was introduced into the P301L construct that destroys a diagnostic SmaI restriction site. The cDNA was conferred with a Kozak consensus sequence and was subcloned into a murine Thy.1.2 genomic expression vector. The vector sequences of this construct (named pR5) were removed prior to microinjection. Transgenic mice were produced by pronuclear injection of B6D2F1×B6D2F1 embryos. Founders were identified by PCR analysis of lysates from tail biopsies using two different primer pairs. Founder animals were intercrossed with C57BL/6 mice to establish lines. Transgenic mice were screened with the following oligonucleotides: tau-I: 5'-GGAGTTCGAAGTGATGGAAG-3' and tau-K: 5'-GGTTTTTGCTGGAATCCTGG-3'. Amplification yielded a product of 500 bp. A restriction digest of the amplification product by SmaI confirmed the presence of the P301L transgene. Of ten independent transgenic lines, four had comparable expression levels as determined by immunoblot analysis. Line pR5-183 was used in the present study.

(ii) Production of Aβ42 and reverse Aβ42-1 fibrils: $A\beta_{42}$ (Bachem, No. H-1368, Lot No. 524548) and $A\beta_{42-1}$ (Bachem, No. H-3976, Lot No. 536763) were reconstituted in PBS at final concentrations of 250 µM, shaken at 1000 rpm for 84 hours at 37° C. in an Eppendorf thermomixer and analyzed by electron microscopy. Preparations were placed on carbon-coated 300-mesh grids and stained with 2% phosphotungstic acid. The preparation of the reverse peptide $A\beta_{42-1}$ consisted of insoluble aggregates that were not readily detectable by negative contrasting in electron microscopy (FIG. 2B). Micrographs were recorded at an operating voltage of 80 to 100 kV and at nominal magnifications of ×40,000 on a Philips model CM12 electron microscope.

(iii) Stereotaxic injection: Stereotaxic injections into mouse brain were carried out according to the protocols of Paxinos (Paxinos K B, The mouse brain in stereotaxic coordinates, Academic Press, San Diego, 1997). Mice were anaesthesized with a mixture of 2% Xylazin and 10% Ketamin, and stereotaxically injected with 1.5 µl of peptide suspension into the CA1 region of the hippocampal formation of the right hemisphere (coordinates: AP −1.9 mm from the bregma, LAT −1.0 mm, DV +1.9 mm), and into the cortex of the left hemisphere (coordinates: AP −1.9 mm from the bregma, LAT +2.0 mm, DV +1.2 mm; includes the trunk region of the somatosensory cortex 1, S1Tr), using a 10 µl Hamilton syringe driven by a mini pump (Motorized Stereotaxic Injector, Stoelting Co.), with an injection speed of 0.15 µl/min. The needle was kept in the injection site for another ten minutes, and then slowly withdrawn. Operated animals were kept under daily control. No mouse developed infections or died during the experiment. Injected mice were perfused transcardially with 4% paraformaldehyde in sodium phosphate buffer, pH 7.4, on days 18, 26, 45 and 60, respectively, and processed for immunohistochemistry. To determine axonal uptake, we injected 1.5 µl of 12.5 mg/ml Texas red-coupled dextran (70,000 MW, Molecular Probes) in PBS, and perfused the mice five to eight days later.

(iv) Immunohistological stainings, immunofluorescence analysis and antibodies: Immunohistological stainings were performed on 4 µm coronal paraffin sections from brain, by using standard published procedures. Serial frontal sections were taken, and brain sections from AD patients and healthy humans were included as controls. Some of the sections were pretreated with 5 µg/ml proteinase K in Tris-buffered saline or PBS at 37° C. for 2.5 minutes for signal enhancement. Sections were stained with thioflavin-S and silver-impregnated by the Gallyas protocol (Gallyas F, Acta Morphol Acad Sci Hung 1971, 19:1). For Gallyas stainings, every $20^{th}$ section was analyzed from positions AP −1.5 mm to AP −2.4 mm (from the bregma), whereas every fifth section was analyzed around the injection site (position AP −1.9 mm) from positions AP −1.8 mm to AP −2.0 mm. Gallyas-positive NFTs were counted in 20 standardized frontal sections of total brain from each mouse, and added. Averages and standard deviations were determined for the numbers of mice indicated in FIG. 8. Tau14 (Zymed Inc, South San Francisco, Calif., amino acids 83-120, used at 1:2 dilutions) and HT7 (Innogenetics Inc, Belgium, amino acids 159-163, 1:200) were used to detect human tau specifically. The following antibodies were used to detect distinct tau phospho-epitopes (in brackets): AT270 (Innogenetics Inc., 1:500, threonine 181), AT8 (Innogenetics Inc., 1:50, serine 202/threonine 205), AT100 (Innogenetics Inc., 1:100, serine 212/threonine 214), 12E8 (Dr. Peter Seubert, 1:100, serine 262/serine 356), AT180 and TG3 (Dr. Peter Davies, 1:100 and 1:20, resp., threonine 231/serine 235), PHF1 (Dr. Peter Davies, 1:50); S199P (Dr. Andre Delacourte, 1:100, serine199), R145d (Dr. Khalid Iqbal, 1:30, serine422) and $pS^{422}$ (Biosource Inc., 1:50, serine422), and AD2 (Dr. Chantal Mourton-Gilles, 1:10.000, serine 396/serine 404). MC1 detected the conformational Alz-50 epitope (Dr. Peter Davies, 1:20). Monoclonal antibody 6E10 (Serotec, 1:500) was used to detect Aβ peptide. Anti-GFAP polyclonal antibody (Sigma, 1:400), was used to detect activated astrocytes and Isolectin B4 (Vector Laboratories, 2 μg/ml) was used to detect microglia. Secondary antibodies were obtained from Vector Laboratories (Vectastain ABC kits PK-6101 and PK-6102) for peroxidase/DAB stainings, and from Molecular Probes (ALEXA-FLUOR series) for immunofluorescence.

(v) Transmission electron microscopy: Areas containing the amygdala were excised from 40-μm-thick vibratome sections and fixed in 4% paraformaldehyde and 0.1% glutaraldehyde in PBS. After fixation with OsO4, tissue samples for routine electron microscopy were embedded in epoxy resin (Epon, Sigma, Bornem, Belgium). For immunogold labeling, ultrathin sections from epoxy-resin-embedded tissues on formvar-coated nickel grids were treated with 6% sodium metaperiodate for 10 minutes and with 5% normal goat serum in PBS for 30 minutes. This was followed by incubating the sections with monoclonal antibody AT8 in 1% normal goat serum in PBS at a dilution of 1:50 for 2 hours. After washing, 10-nm colloidal gold-tagged secondary antibody in Tris-buffered saline (goat anti-mouse; British Biocell, Cardiff, UK) was applied for 1 hour. Then, after washing, sections were stained with lead citrate and uranyl acetate. Control sections were stained following the same procedure, but with omission of the primary antibody. AT8 appeared to label frequently "ends" of filaments due to the fact that filaments sectioned at the surfaces of the epoxy-embedded preparations were more easily accessible for the antibodies than deeper layers.

The invention claimed is:

1. A method of increasing the number of neurofibrillary tangles in a transgenic mouse having a genome comprising a DNA sequence encoding a mutant tau protein operably linked to a promoter by injection of APP or a β-amyloid fragment thereof into the brain of the mouse.

2. The method of claim 1 wherein increasing the number of neurofibrillary tangles is by injection of the β-amyloid fragment of APP.

3. The method according to claim 2 wherein the β-amyloid fragment of APP is $A\beta_{42}$.

4. The method according to claim 3 wherein the $A\beta_{42}$ is fibrillar, pre-aggregated, or aggregated.

5. A method of accelerating the production of neurofibrillary tangles in a transgenic mouse having a genome comprising a DNA sequence encoding a mutant tau protein operably linked to a promoter by injection of APP or a β-amyloid fragment thereof in the brain of the mouse.

6. The method of claim 5 by injection of the β-amyloid fragment of APP.

7. The method according to claim 1 wherein the mutant tau is a human mutant tau.

8. The method according to claim 1 wherein the mutant tau is P301L mutant tau.

9. The method according to claim 2 wherein the β-amyloid fragment of APP is injected into the hippocampus or the cortex of the brain.

10. The method according to claim 2 wherein the APP is a mutant APP.

11. The method according to claim 1 wherein the increase of neurofibrillary tangles is predominantly in the amygdala of the brain.

12. The method according to claim 1 wherein the increase of neurofibrillary tangles is predominantly in the basolateral amygdala of the brain.

13. The method according to claim 1 wherein the increase of neurofibrillary tangles is at least two-fold, as compared to a control mouse to which no APP or a β-amyloid fragment thereof has been injected.

14. The method according to claim 1 wherein the increase of neurofibrillary tangles is at least five-fold as compared to a control mouse to which no APP or a β-amyloid fragment thereof has been injected.

15. The method according to claim 1 for inducing neuropil threads and/or degeneration of neurites.

16. A transgenic mouse obtained by injecting into the brain of a mouse a polypeptide selected from the group consisting of APP and a β-amyloid fragment thereof in an amount sufficient to induce the production of neurofibrillary tangles, the mouse having a genome comprising a DNA sequence encoding a mutant tau protein operably linked to a promoter.

17. The transgenic mouse according to claim 16 wherein the polypeptide is the β-amyloid fragment of APP.

18. The transgenic mouse according to claim 17 wherein the β-amyloid fragment of APP is injected into the hippocampus or the cortex of the brain.

19. The transgenic mouse according to claim 16 wherein the mouse expresses a recombinant gene for APP or the β-amyloid fragment thereof, the APP being enzymatically processed to generate a cleavage product.

20. The transgenic mouse according to claim 19 wherein the cleavage product is β-amyloid.

21. The transgenic mouse according to claim 19 wherein the APP is a mutant APP.

22. A method to determine or validate the efficacy of a modulating agent or therapy, comprising
administering to the transgenic mouse of claim 16 a modulating agent or therapy and
determining the effect of the agent or therapy on amyloid lowering or NFT reduction.

23. The method according to claim 22 wherein the modulating agent or therapy is for a neurodegenerative disease, frontotemporal dementia (FTD), or other neurodegenerative disease accompanied by neurofibrillary tangle formation.

24. The method according to claim 22 wherein the modulating agent or therapy is for Alzheimer's disease.

* * * * *